United States Patent [19]

Vaughan

[11] 4,188,308

[45] Feb. 12, 1980

[54] CONVERSION OF PENDANT SULFONATE GROUPS TO SULFONIC ACID GROUPS ON PERFLUORVINYLETHER-TETRAFLUORO-ETHYLENE COPOLYMER CATALYSTS

[75] Inventor: Ronald J. Vaughan, Orinda, Calif.

[73] Assignee: Varen Technology, Marshallton, Del.

[21] Appl. No.: 904,503

[22] Filed: May 10, 1978

Related U.S. Application Data

[63] Continuation-in-part of Ser. No. 660,634, Feb. 23, 1976.

[51] Int. Cl.$^2$ .............................................. B01J 31/40
[52] U.S. Cl. .................................... 252/413; 252/415; 252/431 R; 252/426; 252/430; 585/477; 585/486; 526/243; 526/247
[58] Field of Search ............ 252/413, 415, 426, 431 R, 252/430, 428

[56] References Cited

U.S. PATENT DOCUMENTS

| 3,282,875 | 11/1966 | Connolly et al. ................... 526/247 |
| 3,624,053 | 11/1971 | Gibbs ................................... 526/243 |

FOREIGN PATENT DOCUMENTS 733753  7/1955  United Kingdom ................ 260/683.47

*Primary Examiner*—P. E. Konopka

[57] ABSTRACT

This invention relates to a method for preparing an acid catalyst which comprises contacting a copolymer of perflurovinyl ether and tetrafluoroethylene containing pendant sulfonate groups with a strong acid having a pKa of less than 1 to convert said sulfonate groups into sulfonic acid groups, removing the excess strong acid and salt formed from such conversion, preferably by washing said sulfonic acid group containing polymer with a solvent in which said salt and said acid are soluble, and removing said solvent from said sulfonic acid group containing polymer. Preferably the strong acid is nitric acid, e.g., aqueous nitric acid, and said solvent is aqueous. The excess solvent may be removed by drying at a temperature of from 50 to 200 degrees C., preferably at reduced pressures. The use of the catalyst prepared by this method for isomerization of hydrocarbons, e.g., xylene, and dealkylation of alkylbenzenes, e.g., diethylbenzene and diisopropylbenzene are also claimed.

2 Claims, No Drawings

CONVERSION OF PENDANT SULFONATE GROUPS TO SULFONIC ACID GROUPS ON PERFLUORVINYLETHER-TETRAFLUOROETHYLENE COPOLYMER CATALYSTS

This patent application is a continuation in part of U.S. Ser. No. 660,634 filed on Feb. 23, 1976 in the name of Ronald J. Vaughan.

FIELD OF THE INVENTION

This invention relates to a method for preparing an acid catalyst which comprises contacting a copolymer of perfluorovinylether and tetrafluorethylene containing pendant sulfonate groups with a strong acid having a pka of less than 1 to convert said sulfonate groups into sulfonic acid groups, removing the excess strong acid and salf formed from such conversion, preferably by washing said sulfonic acid group containing polymer with a solent in which said salt and said acid are soluble, and removing said solvent from said sulfonic acid group containing polymer. Preferably, the strong acid is nitric acid, e.g., aqueous nitric acid, and said solvent is aqueous. The excess solvent may be removed by drying at a temperature of from 50° to 200° C., preferably at reduced pressures. The use of the catalyst prepared by this method for isomerization of hydrocarbons, e.g., xylene and dealkylation of alkylbenzenes, e.g., diethylbenzene and diisopropylbenzene are also claimed.

SUMMARY OF THE INVENTION

It has now been unexpectedly found that an acidic hydrocarbon conversion catalyst, useful in isomerization, alkylation, dealkylation, polymerization, and other processes involving the conversion of hydrocarbons by contacting said hydrocarbons with an acidic catalyst, may be prepared by contacting a copolymer of perfluorovinylether and tetrafluoroethylene containing pendant sulfonate groups with a strong acid having a pKa of less than 1 to convert said sulfonate groups into sulfonic acid groups, removing the excess strong acid and salt formed from such conversion, preferably by washing said sulfonic acid group containing polymer with a solvent in which said salt and said acid are soluble, and removing said solvent from said sulfonic acid group containing polymer.

This novel method is also useful in activating said catalyst after it has become deactivated by use in a hydrocarbon conversion process, e.g., by neutralization of said sulfonic acid groups, coating of the catalyst surface with tar-like reaction products, etc.

It has also been found that the isomerization of alkyl aromatics such as xylenes and dealkylation of polyalkyl aromatics such as diethyl and diisopropylbenzenes is unexpectedly improved by conversion in the presence of the above catalyst especially when treated according to the instant method.

In general, the above-noted catalyst is available as the neutralized copolymer, i.e., as the potassium or salt, and must be converted to the acid form prior to use. It has been found that unless the above-described method is utilized, the activity of such catalyst is not sufficient to give the yields and selectivity required in a commercial hydrocarbon conversion process. Therefore, the neutralized copolymer (or the above-described deactivated catalyst) is activated by contacting with a strong acid having a pKa of less than 1, preferably less than 0, at conditions sufficient to convert the neutralized sulfonic acid groups into the acid form. Said contacting can be carried out in the liquid or vapor phase although it is generally preferred that a liquid phase capable of dissolving or dispersing any of the byproducts of such activation such as salts, tars, etc., be used. The liquid phase will be selected with regard to the solubility of the catalyst therein since it is not desirable to dissolve such catalyst in the liquid phase. Due to the insoluble nature of the copolymer in the strong acids useful in activation of the catalyst, selection of the liquid phase is not difficult.

In general, strong acids such as HCl, HBr, $H_2SO_4$ and $HNO_3$ may be used provided they are within the above-noted pKa limitation. These acids are generally used as their aqueous solutions, therefore, substantially any salt formed by interaction of said acids with the neutralized copolymer will be soluble in the strong acid solution.

It has been found that nitric acid, e.g., 70% $HNO_3$ by weight in water, is especially preferred when utilizing the instant method to activate catalysts which have become deactivated during use in a hydrocarbon conversion process. The nitric acid is very efficient in removing any tars from the catalyst surface in addition to being suitable for converting the neutralized sulfonic acid groups into the acid form and dissolving the byproduct salts of such conversion.

The neutralized copolymer (or the deactivated catalyst) may be contacted with the strong acid at a temperature of up to about 200° C. or higher. Preferably, such contacting is carried out at a temperature of from about 50° to 150° C.

This contacting step may be carried out at any convenient pressure; however, as noted above, it is desirable to provide sufficient pressure to maintain the strong acid in the liquid phase. In general, atmospheric pressure may be used.

The contacting of said neutralized copolymer or said deactivated catalyst is carried out for a time sufficient to convert substantially all of the neutralized sulfonic acid groups to the acid form at the temperature, acid strength, etc. chosen. Generally said contacting is carried out for from 10 to 60 minutes. However, if the surface of the deactivated catalyst is coated with tar a contacting time sufficient in duration to assure that the sulfonic acid groups will be available for catalysts during the subsequent use of said catalyst may be required. As noted above, nitric acid appears to be especially efficient in activating such deactivated catalysts, therefore, the contacting time of the deactivated catalyst with such acid may be from 10 to 60 minutes also.

The catalyst which is activated by the process of the instant invention may be in various physical forms, that is it may be fabricated into sheets, hollow tubes, granules having a particle size of from 6 mesh to less than 400 mesh, fibers, etc. The catalyst may be supported or unsupported, e.g., the catalyst can be coated onto a metal having good heat exchanger properties. It will be obvious to the skilled artisan that variations in the conditions of the above contacting step, i.e., time, temperature and pressure, may be necessitated by the form of the catalyst. However, such variations are easily within the skill of the art.

After the neutralized sulfonic acid groups are converted in the above-described step, it is necessary to remove excess acid and the byproducts of such conversion. When the conversion is carried out in the liquid phase, a majority of the excess acid and said byproduct is removed merely by separating the solid copolymer from the liquid. It is generally necessary to wash said separated copolymer with additional liquid to remove any trace of said excess acid and said byproducts. Conveniently, water is used for such washing for the purpose of economy, as well as its ability to solubilize excess acid and dissolve or disperse said byproducts.

The solid copolymer may be washed with fresh water until the wash water has a pH of 4 or greater.

It should be noted that if the above contacting step is carried out in the vapor phase, it may be more difficult to remove excess acid and byproducts than if the liquid phase is used since substantially all the byproduct salt will remain on the catalyst surface at the conclusion of said contacting step.

After washing, the excess liquid must be removed from the catalyst. A drying step carried out at elevated temperatures and/or reduced pressures is suitable for removing the excess liquid. The catalyst may also be dried in an inert gas or contacted with a hydrocarbon feed stock for a time sufficient to remove such excess liquid. In general, drying temperatures of at least 120° C. preferably from 140° to 180° C. and pressures of from 0.10 mm to atmospheric may be used. The drying may be carried out for a time sufficient to remove excess liquid down to a level of 10 ppm on said catalyst. Heating at 180 degrees C. and a pressure of 0.10 mm Hg, e.g., for a period of 2 to 6 hours is generally sufficient to dry the catalyst.

The above method for activating a solid acid hydrocarbon conversion catalyst has been described with reference to a particular copolymer, however, this method is also suitable for activating any poly fluorosulfonic acid catalyst which is a fluorocarbon polymer containing pendant sulfonic acid and is derived from fluorocarbon polymers having mixed chlorine and fluorine substituents, wherein the number of chlorine atoms is not more than about 20% of the total chlorine and fluorine atoms present in said polymer. The perfluorinated derivatives of these materials are particularly suitable for the process of the instant invention and said perfluorocarbon polymer may have the pendant sulfonic acid attached either directly to the main polymer chain or to perfluorocarbon side chains which are attached to the main polymer chain. Either or both of the main polymer chain and the side chain may contain oxygen atom linkages, such as ether linkages, for example, as in Nafion, perfluorosulfonic acid membrane obtained from E. I. duPont de Nemours and Company. The perfluorocarbon polymer particularly suitable for use in the method of the instant invention may be prepared as disclosed in U.S. Pat. Nos. 3,041,317; 3,282,875; and 3,624,053, hereby incorporated by reference. However as noted above, the most preferred polymers are prepared by copolymerizing a perfluorovinyl ether having the formula:

FSO$_2$CF$_2$OCF(CF$_3$)CF$_2$OCF=CF$_2$ and tetrafluoroethylene followed by conversion of the SO$_2$F group to a sulfonic acid group. The equivalent weight of the preferred copolymer preferably ranges from 850 to 2500 where the equivalent weight is defined as the average molecular weight per sulfonyl group.

The catalysts prepared by the method of the instant invention are especially suitable for dealkylation or alkylaromatics such as diethyl benzene and diisopropyl benzene and isomerization of alkylaromatics such as xylene isomers. In the former reaction, the resulting products may be the mono alkylate, i.e., ethyl benzene and isopropyl benzene, respectively, and in the latter reaction, the product is a mixture of xylene isomers having a different distribution than the starting material.

In the processes noted above, the following reaction parameters may conveniently used: the hydrocarbon starting material, e.g., xylene, diethylbenzene, etc, is contacted with the catalyst at a temperature of from 0 to 200 degrees C., preferably from 50 to 190 degrees C. and a pressure of from 0 psig to 1000 psig, preferably from 0 psig to 150 psig although the specific operating pressures and temperatures will relate to the specific hydrocarbon which is to be converted. In general, the pressure is adjusted so as to keep the hydrocarbon in in the liquid phase at the catalyst operating temperature. The temperature is chosen so as to provide a convenient conversion rate while minimizing tar formation on the catalyst. The hydrocarbon feed rates are preferably adjusted so as to provide substantially complete conversion in the time of passage through the catalyst zone, although it may be desirable from a selectivity standpoint to provide partial conversion in the catalyst zone.

The presence of moisture and other impurities should be avoided in carrying out the above process since catalyst activity and life may be decreased. For similar reasons basic material should also be excluded from contact with the reactants and the catalyst during the conversion processes. For example, amines, inorganic bases, e.g., NaOH, sulfur compounds, for example CH$_3$SH, CH$_3$—S—S—CH$_3$ should be carefully excluded. The skilled artisan will especially appreciate that no more than 0.05 wt. % water, preferably no more than 0.01 wt. % water, should be present in the reactant feed streams.

The following are specific embodiments of the instant invention. However, there is no intent to be bound thereto since many changes will be obvious to those skilled in the art with the instant specification before them. Such obvious changes are intended to be within the scope of the appended claims.

The examples below utilize methodology and reactors disclosed in my copending U.S. Ser. No. 660,634, filed Feb. 23, 1976 the parent application, which is hereby incorporated by reference for such disclosure.

EXAMPLE 1

(A) A stainless steel tube (304 ss, 35"×0.25" O.D.×0.20" I.D.) was filled with a bundle of fine (less than 0.001" diameter) Nafion fiber (13.14 g, equilibrated with atmospheric humidity, 1200 E.W.). End fittings and check valves were attached to the tube and the assembly was placed in a forced-fan oven at 110 degrees C. Nitric acid (70%) was pumped through at 0.5 ml/min. until several tube volumes had passed though. Water was then pumped through (1ml/min.) at 100 degrees until the effluent indicated a pH greater than 4. Dry nitrogen was then passed through the reactor at 140 degrees C. for several hours at 20 ml/min. until the reactor reached a constant weight. This reactor was used in Example 2 below.

(B) Granular Nafion resin (20–40 mesh, 10.0 g as potassium salt) was immersed in nitric acid (70%) in a beaker and boiled gently on a hot plate for one hour. The nitric acid was decanted from the resin and replaced with fresh nitric acid and boiled again for one hour. This process was repeated once more, then the resin was boiled with several changes of distilled water until the pH of the decanted solution was greater than 4. The damp resin was placed into a stainless-steel tube and connected to a source of vacuum. The tube was maintained at 165 degrees C. at 0.2 mm Hg overnight, by which time the tube had reached constant weight.

EXAMPLE 2

Dealkylation of Diisopropylbenzene

A solution (10% w/v in dry benzene) of freshly distilled diisopropylbenzene (E.K., mixed isomers) was pumped through Reactor #1 at a flow rate of 0.28 ml/min. Check valves on the outlet maintained the reactor contents as liquid. Samples were taken at increasing temperatures and analyzed (Table I). At the highest temperature investigated (121°), the flow rate was increased to a maximum of 0.86 ml/min. The reactor was then allowed to stand overnight to obtain a sample which had been completely equilibrated #24 (Table II). It can readily be seen that equilibration of the mixture of isopropyl and diiopropylbenzene is essentially complete at temperatures greater than 110° at 0.28 ml/min, and up to about 0.7 ml/min at 120°; this corresponds to a total residence time in the catalyst region of about 20 min.

EXAMPLE 3

Dealkylation of Diethylbenzene

Dealkylation of diethylbenzene, as expected from the alkylation results, was somewhat less efficient (using the same reactor design) (Table III).

TABLE I

Dealkylation of Diisopropylbenzene in the Presence of Excess Benzene Catalyzed by Nafion ™
The Flow Rate of the 10% w/v Diisopropylbenzene in Benzene was 0.28 ml/min. Reactor #1

| # | T (°C.) | Isopropylbenzene, % wt/vol | Diisopropylbenzene(s) (% wt/vol) |
|---|---|---|---|
| 4 | 50 | 0.09 | 9.5 |
| 5 | 64 | 0.27 | 10.3 |
| 7 | 79 | 1.94 | 8.9 |
| 9 | 93 | 5.73 | 6.5 |
| 11 | 100 | 8.37 | 4.3 |
| 13 | 110 | 11.84 | 1.4 |
| 15 | 121 | 11.87 | 0.82 |

TABLE II

Conditions as in Table I; T = 21° C. Flow Rate as Indicated

| # | Flow Rate (ml/min) | Isopropylbenzene % wt/vol | Diisopropylbenzene % wt/vol |
|---|---|---|---|
| 15 | 0.28 | 11.87 | 0.82 |
| 17 | 0.39 | 12.00 | 1.23 |
| 19 | 0.56 | 10.84 | 1.2 |
| 22 | 0.86 | 10.57 | 2.7 |
| 24 | 0 | 10.25 | 0.44 |

TABLE III

Dealkylation of a Diethylbenzene (Koppers Co., Mixed Isomers 5% wt/vol in Dry Benzene); the Flow Rate was 0.39 ml/min using Reactor #9

| # | T °C. | Ethylbenzene, % wt/vol | Diethylbenzene, % wt/vol |
|---|---|---|---|
| 5 | 70 | 0.22 | 4.52 |
| 8 | 90 | 0.57 | 4.16 |
| 10 | 104 | 0.50 | 4.38 |
| 12 | 120 | 1.00 | 4.03 |
| 14 | 140 | 2.03 | 3.30 |

EXAMPLE 4

Isomerization of Xylene

Reactor #1 was cycled in the usual manner and dried with nitrogen at 170°. Check valves of 10 psi and 25 psi cracking pressures were attached to the inlet and outlet (respectively) of the reactor. p-Xylene was introduced at 0.56 ml/min at 59°. Samples were taken at increasing temperatures, in every case allowing more than a reactor volume of p-xylene to pass through the reactor before taking a sample for analysis by gas chromatography. The results are presented in Table IV. After the sample at 161° was taken, the reactor was allowed to stand at 161° for an additional 6 hours, then cooled to room temperature and allowed to stand two days; Sample #11 was taken on resumption of xylene flow at room temperature.

TABLE IV

Isomerization of p-Xylene Catalyzed by Nafion ™
Reactor #1, Flow Rate 0.56 ml/min of p-xylene
"%" is Integration Ratio

| # | T (°C.) | Toluene (%) | p-Xylene (%) | m-Xylene (%) | o-Xylene (%) |
|---|---|---|---|---|---|
| 2 | 59 | — | 100 | — | — |
| 4 | 79 | — | 100 | — | — |
| 6 | 100 | — | 100 | — | — |
| 8 | 139 | 3.3 | 91.3 | 5.3 | — |
| 10 | 161 | 2.6 | 85.7 | 11.7 | Trace |
| 11 | 161–6 hr | 11.7 | 57.3 | 24.8 | 6.2 |

What is claimed is:

1. A method for reactivating a deactivated acid catalyst comprising a copolymer of perfluorovinyl ether and tetrafluoroethylene, said copolymer catalyst containing pendant sulfonic acid groups, said catalyst having become deactivated by use in a hydrocarbon conversion process, which reactivating method comprises contacting said deactivated catalyst with strong nitric acid to remove contaminants and to convert sulfonate groups into sulfonic acid groups, removing excess nitric acid and salt formed from such conversion by water washing said sulfonic acid group containing copolymer until the wash water has a pH above 4 and drying the washed acid copolymer catalyst at 50° to 200° C.

2. The method of claim 1 wherein said strong nitric acid is aqueous 70% nitric acid.

* * * * *